(12) United States Patent
Chaves et al.

(10) Patent No.: US 11,617,825 B2
(45) Date of Patent: Apr. 4, 2023

(54) FLUID PATH CHANNEL AND ADSORBENT

(71) Applicant: Becton, Dickinson and Company, Franklin Lakes, NJ (US)

(72) Inventors: Alex Chaves, Tyngsboro, MA (US); Emilie Mainz, Malden, MA (US); Richard Bucchianeri, Westford, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 284 days.

(21) Appl. No.: 16/687,024

(22) Filed: Nov. 18, 2019

(65) Prior Publication Data

US 2020/0155755 A1 May 21, 2020

Related U.S. Application Data

(60) Provisional application No. 62/769,780, filed on Nov. 20, 2018.

(51) Int. Cl.
*A61M 5/142* (2006.01)
*A61M 5/168* (2006.01)
(Continued)

(52) U.S. Cl.
CPC ........ *A61M 5/142* (2013.01); *A61M 5/16831* (2013.01); *A61M 5/204* (2013.01);
(Continued)

(58) Field of Classification Search
CPC .. A61M 5/142; A61M 5/16831; A61M 5/204; A61M 5/165; A61M 5/14248;
(Continued)

(56) References Cited

U.S. PATENT DOCUMENTS 2,571,059 A 10/1951 Puschelberg et al.
5,217,627 A * 6/1993 Pall ..................... A61M 1/0218
604/6.02

(Continued)

FOREIGN PATENT DOCUMENTS

EP 2164614 A2 3/2010
WO 200112746 A1 2/2001
WO WO-2016048878 A1 * 3/2016 ........ A61M 5/14248

OTHER PUBLICATIONS

Extended European Search Report dated Dec. 20, 2019, which issued in the corresponding European Patent Application No. 19208304.6.

*Primary Examiner* — James D Ponton
*Assistant Examiner* — Neeraja Gollamudi
(74) *Attorney, Agent, or Firm* — Dickinson Wright PLLC

(57) ABSTRACT

A delivery device for delivering medicament, such as insulin, to a patient includes a housing and a base enclosing an inner cavity. Enclosed within the housing is a reservoir for containing a medicament, a delivery mechanism for delivering the medicament to the patient, and a pump in fluid communication with the reservoir and delivery mechanism. The base has an integrally formed fluid channel in fluid communication with the reservoir and the delivery mechanism and a filter media containing an adsorbent positioned in the fluid channel to contact the medicament and remove at least a portion of a stabilizing compound from the medicament carried through the fluid channel.

25 Claims, 10 Drawing Sheets

(51) Int. Cl.
*A61M 5/20* (2006.01)
*A61K 38/28* (2006.01)

(52) U.S. Cl.
CPC .......... *A61K 38/28* (2013.01); *A61M 2205/75* (2013.01); *B01D 2253/102* (2013.01)

(58) Field of Classification Search
CPC ...... A61M 2205/75; A61M 2205/3331; A61M 2005/1652; A61K 38/28
See application file for complete search history.

(56) References Cited

U.S. PATENT DOCUMENTS

| | | | |
|---|---|---|---|
| 5,693,018 A | 12/1997 | Kriesel | |
| 5,776,103 A * | 7/1998 | Kriesel | A61M 5/152 128/DIG. 12 |
| 2009/0012472 A1 * | 1/2009 | Ahm | A61M 5/158 604/138 |
| 2016/0354542 A1 * | 12/2016 | Ward | A61B 5/14532 |
| 2018/0272058 A1 * | 9/2018 | Pizzochero | A61M 5/1413 |
| 2019/0054233 A1 * | 2/2019 | Demaria | A61M 5/165 |

* cited by examiner

FLUID PATH CHANNEL AND ADSORBENT

This application claims priority to U.S. Provisional Patent Application Ser. No. 62/769,780, filed on Nov. 20, 2018, which is hereby incorporated by reference in its entirety.

FIELD OF THE INVENTION

The present invention relates to medical devices, and more particularly, to a medicament delivery device with at least one fluid channel having an adsorbent or filter media where the channel directs the medicament, such as insulin, to a delivery mechanism for delivering the medicament to a patient.

BACKGROUND OF THE INVENTION

Diabetes is a group of diseases characterized by high levels of blood glucose resulting from the inability of diabetic patients to maintain proper levels of insulin production when required. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient. Type 1 diabetes (T1D) patients are required to take insulin (e.g., via injections or infusion) to move glucose from the bloodstream because their bodies generally cannot produce insulin. Type 2 diabetes (T2D) patients generally can produce insulin but their bodies cannot use the insulin properly to maintain blood glucose levels within medically acceptable ranges. In contrast to people with T1D, the majority of those with T2D usually do not require daily doses of insulin to survive. Many people are able to manage their condition through a healthy diet and increased physical activity or oral medication. However, if they are unable to regulate their blood glucose levels, they will be prescribed insulin. For example, there are an estimated 6.2 million Type 2 diabetes patients (e.g., in the United States, Western Europe and Canada) taking multiple-daily-injections (MDI) which consist of a 24-hour basal insulin and a short acting rapid insulin that is taken at mealtimes for glycemic management control.

For the treatment of Type 1 diabetes (T1D) and sometimes Type 2 diabetes (T2D), there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates to more closely match the functions and behavior of a properly operating pancreas of a non-diabetic person that produces the required insulin, and the insulin pump can help the diabetic patient maintain his/her blood glucose level within target ranges based on the diabetic patient's individual needs. Infusion pump therapy requires an infusion cannula, typically in the form of an infusion needle or a flexible catheter, that pierces the diabetic patient's skin and through which infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life. For example, many of the T2D patients who are prescribed insulin therapy can be expected to convert from injections to infusion therapy due to an unmet clinical need for improved control. That is, a significant number of the T2D patients who take multiple-daily-injections (MDI) are not achieving target glucose control or not adhering sufficiently to their prescribed insulin therapy.

Typically, regardless of whether a diabetic patient uses multiple direct injections (MDIs) or a pump, the diabetic patient takes fasting blood glucose medication (FBGM) upon awakening from sleep, and also tests for glucose in the blood during or after each meal to determine whether a correction dose is required. In addition, the diabetic patient may test for glucose in the blood prior to sleeping to determine whether a correction dose is required, for instance, after eating a snack before sleeping.

To facilitate infusion therapy, there are generally two types of insulin pumps, namely, conventional pumps and patch pumps. Conventional pumps use a disposable component, typically referred to as an infusion set, tubing set or pump set, which conveys the insulin from a reservoir within the pump into the skin of the user. The infusion set includes a pump connector, a length of tubing, and a hub or base from which a cannula, in the form of a hollow metal infusion needle or flexible plastic catheter, extends. The base typically has an adhesive that retains the base on the skin surface during use. The cannula can be inserted onto the skin manually or with the aid of a manual or automatic insertion device. The insertion device may be a separate unit employed by the user.

Another type of insulin pump is a patch pump. Unlike a conventional infusion pump and infusion set combination, a patch pump is an integrated device that combines most or all of the fluidic components in a single housing. Generally, the housing is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such patch pumps are replaced on a frequent basis, such as every three days, or when the insulin reservoir is exhausted. Otherwise, complications may occur, such as restriction in the cannula or the infusion site.

As patch pumps are designed to be a self-contained unit that is worn by the patient, preferably, the patch pump is small, so that it does not interfere with the activities of the user. Thus, to minimize discomfort to the user, it would be preferable to minimize the overall thickness of the patch pump. However, to minimize the thickness of the patch pump, the size of its constituent parts should be reduced as much as possible.

In current patch pump designs, tubes, such as plastic tubes, are employed as fluid pathways to route fluid flow from one internal component to another. For example, a tube can connect a medicament reservoir with a delivery needle, but the space required to internally house such a tube adds to the overall size of the patch pump. The use of tubes can increase cost and can result in additional complexity during automated device assembly processes. For example, such device assembly includes connecting the tubes, which adds steps to the assembly process. In addition, preventing leaks from such connections can give rise to additional challenges.

Accordingly, a need exists for an improved fluid path design for use in a limited space environment, such as in a patch pump device, which can cost-effectively transport medicament, while minimizing or reducing the overall size and complexity of the device.

SUMMARY

A feature of the present invention provides a delivery device, such as a patch pump, having at least one fluid channel to administer the medicament to the patient, where the fluid channel has filter media to remove at least a portion of a stabilizer compound from the medicament prior to delivery to the patient. In one embodiment, fluid channels provide a bypass from a wet interface to a dry interface with minimal complexity by routing flow away from the specific interface.

The aspects of the present invention can be achieved by providing a device for delivering medicament into skin of a patient, the device having a housing, which includes a reservoir for housing the medicament A first internal region that is sealed from fluid ingress can include one or more components of the delivery device. A second internal region that is not sealed from fluid ingress can include one or more components of the delivery device. The housing can have a barrier that separates the first internal region and the second internal region. A delivery cannula delivers the medicament into the skin of the patient. In one embodiment, a base has a bottom surface for orienting toward the skin of the patient. The bottom surface of the base has one or more integrally formed fluid channels disposed therein. At least one of the fluid channels contains an adsorbent or filter media in fluid communication with the delivery cannula.

The delivery device can have a housing and a base enclosing the housing to form an internal cavity for receiving the operating components for the delivery device. The delivery device is particularly suitable for delivering insulin at a controlled rate through a cannula or catheter to the patient. The delivery device is shown as a patch pump or infusion pump although the delivery device can have other forms. At least one surface of the housing or the base has an integrally formed fluid channel with a filter media containing an adsorbent positioned in the fluid channel. The channel delivers the insulin from one component of the delivery device to the cannula or catheter where the insulin passing through the channel contacts the adsorbent to remove at least a portion of the stabilizing agents or compounds present in the insulin prior to introducing the insulin to the patient. Reducing the concentration of the stabilizing compounds in the insulin prior to introducing to the patient reduces or inhibits the inflammation and irritation at the injection or infusion site in the patient that often occurs after prolonged delivery of insulin at a single injection site.

The fluid channel can be formed as an open channel that is molded on a surface of the base of the device. The fluid channel has an opening at an inlet end and an opening at the outlet end passing through the base to a side opposite the open channel where the openings can be connected to a component of the device and to the cannula or catheter. A cover member, such as a film or layer is applied to the surface of the base overlying the open channel to enclose the open channel and form the fluid channel. The fluid channel contains the filter media containing the adsorbent where the medicament fluid contacts the adsorbent for removing at least a portion of the stabilizing agents present in the medicament before introducing the medicament to the patient.

In one embodiment, the delivery device for delivering a medicament to a patient includes a housing having an open end and a base coupled to the open end and defining an inner cavity. A reservoir containing the medicament is provided in the cavity of the housing. A delivery mechanism, such as a cannula or catheter, and a pump mechanism are connected to the reservoir. The base has an integrally formed fluid channel having a flow path in fluid communication with the reservoir and the delivery mechanism. A filter media is positioned in the fluid channel for removing at least a portion of a compound from the medicament before delivering the medicament to the delivery mechanism.

The features of the invention are also attained by providing a delivery device for delivering a medicament to a patient where the device includes a housing having an inner cavity and a base enclosing the inner cavity. The housing has an integrally formed fluid channel with an inlet and an outlet. A reservoir is positioned in the cavity for containing a medicament where the medicament contains a stabilizer compound. The reservoir is in fluid communication with the inlet of the fluid channel. The housing includes a delivery mechanism having a cannula for delivering the medicament to the patient where the cannula is in fluid communication with the outlet of the fluid channel. A pump is in fluid communication with the cannula for directing the medicament from the reservoir to the cannula. The fluid channel includes an adsorbent where the medicament passing through the fluid channel contacts the adsorbent and removes at least a portion of the stabilizer compound from the medicament before introducing the medicament to the patient.

Additional and/or other aspects and advantages of the present invention will be set forth in the description that follows, or will be apparent from the description, or may be learned by practice of the invention. The present invention may comprise delivery devices and methods for forming and operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The various aspects and advantages of embodiments of the invention will be more readily appreciated from the following detailed description, taken in conjunction with the accompanying drawings, of which.

DETAILED DESCRIPTION OF EMBODIMENTS

Figure 1:
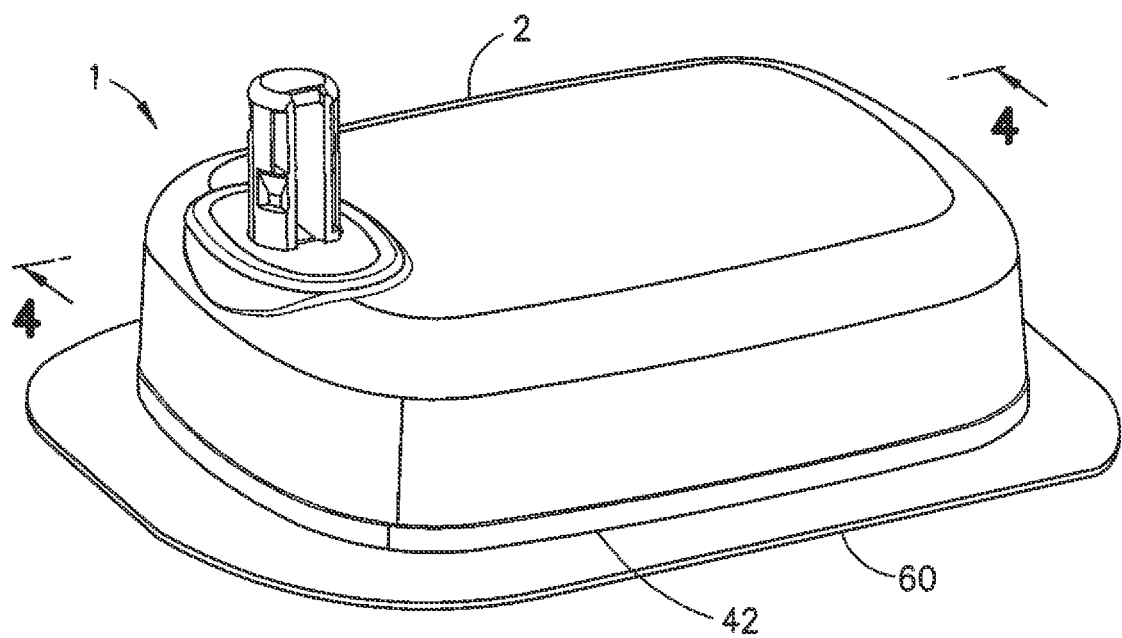
FIG. 1 is a perspective view of a delivery device constructed in accordance with an illustrative embodiment of the present invention.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting. Any of the embodiments and/or elements and features disclosed herein may be combined with one another to form various additional embodiments not specifically disclosed, as long as they do not contradict or are not inconsistent with each other. Terms of degree, such as "substantially", "about" and "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely.

The illustrative embodiments are described with reference to diabetes management using insulin therapy. It is to be understood that these illustrative embodiments can be used with different drug therapies and regimens to treat physiological conditions other than diabetes using different medicaments other than insulin.

Figure 2:
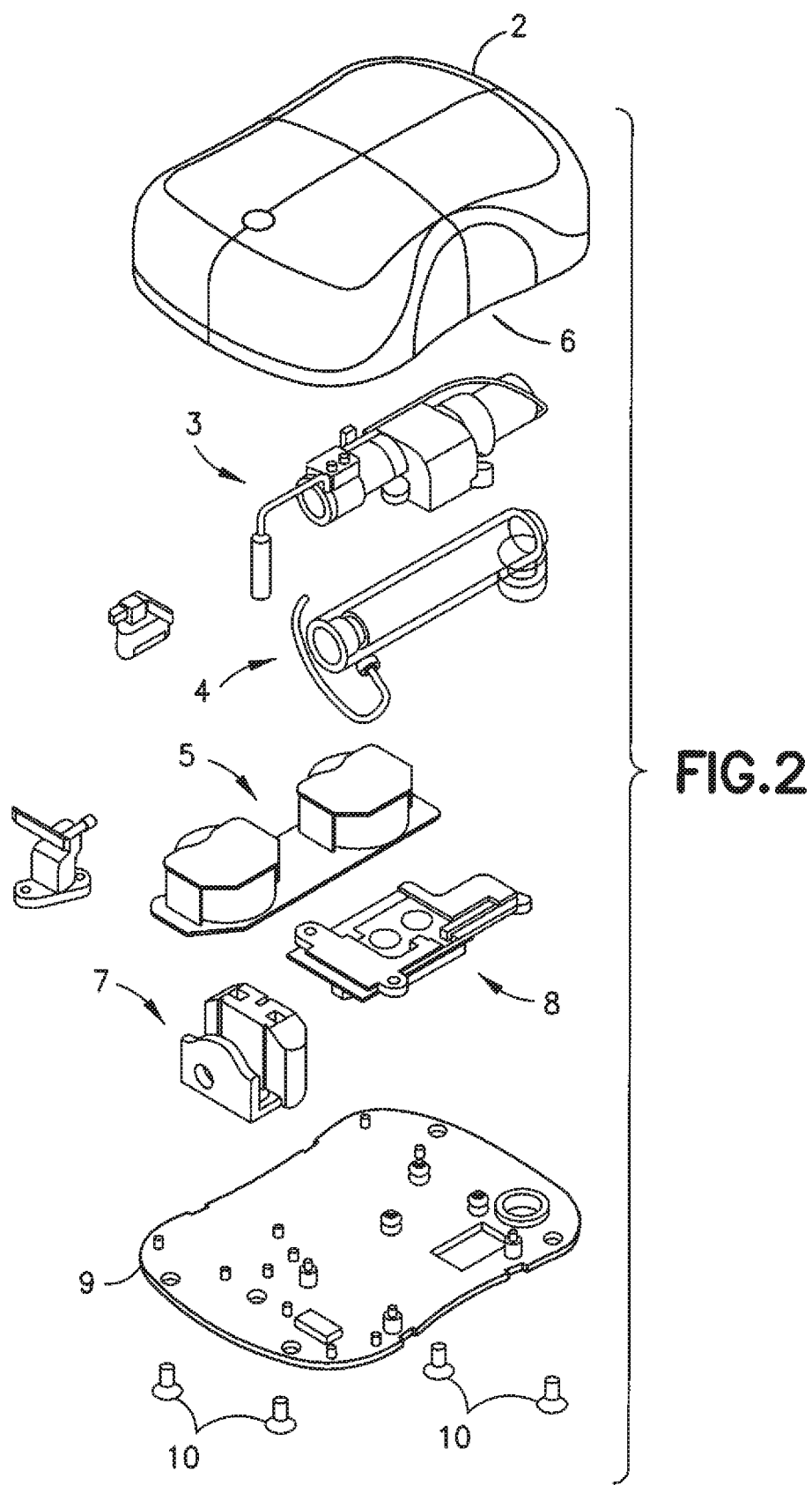
FIG. 2 is an exploded view of the various components of the delivery device of FIG. 1.

FIG. 1 is a perspective view of an exemplary embodiment of a medicament delivery device shown as a patch pump 1. The patch pump as described herein is configured for delivering insulin in the form of an insulin solution to a patient at a controlled rate. FIG. 2 is an exploded view of the various components of the patch pump of FIG. 1, illustrated with a main cover 2. The various components of the patch pump 1 include: a reservoir 4 for storing insulin; a pump 3 for pumping insulin out of the reservoir 4; a power source 5 in the form of one or more batteries; an insertion mechanism 7 for inserting an inserter needle with a cannula 36 into a user's skin; control electronics 8 in the form of a circuit board with optional communications capabilities to outside devices such as a remote controller and computer, including a smart phone; a pair of dose buttons 6 on the cover 2 for actuating an insulin dose, including a bolus dose; and a base to which various components above may be attached via fasteners 10. The patch pump 1 also includes various fluid connector lines that transfer insulin pumped out of the reservoir 4 to the infusion site. The cannula 36 can be a rigid cannula or flexible catheter as known in the art.

Figure 3:
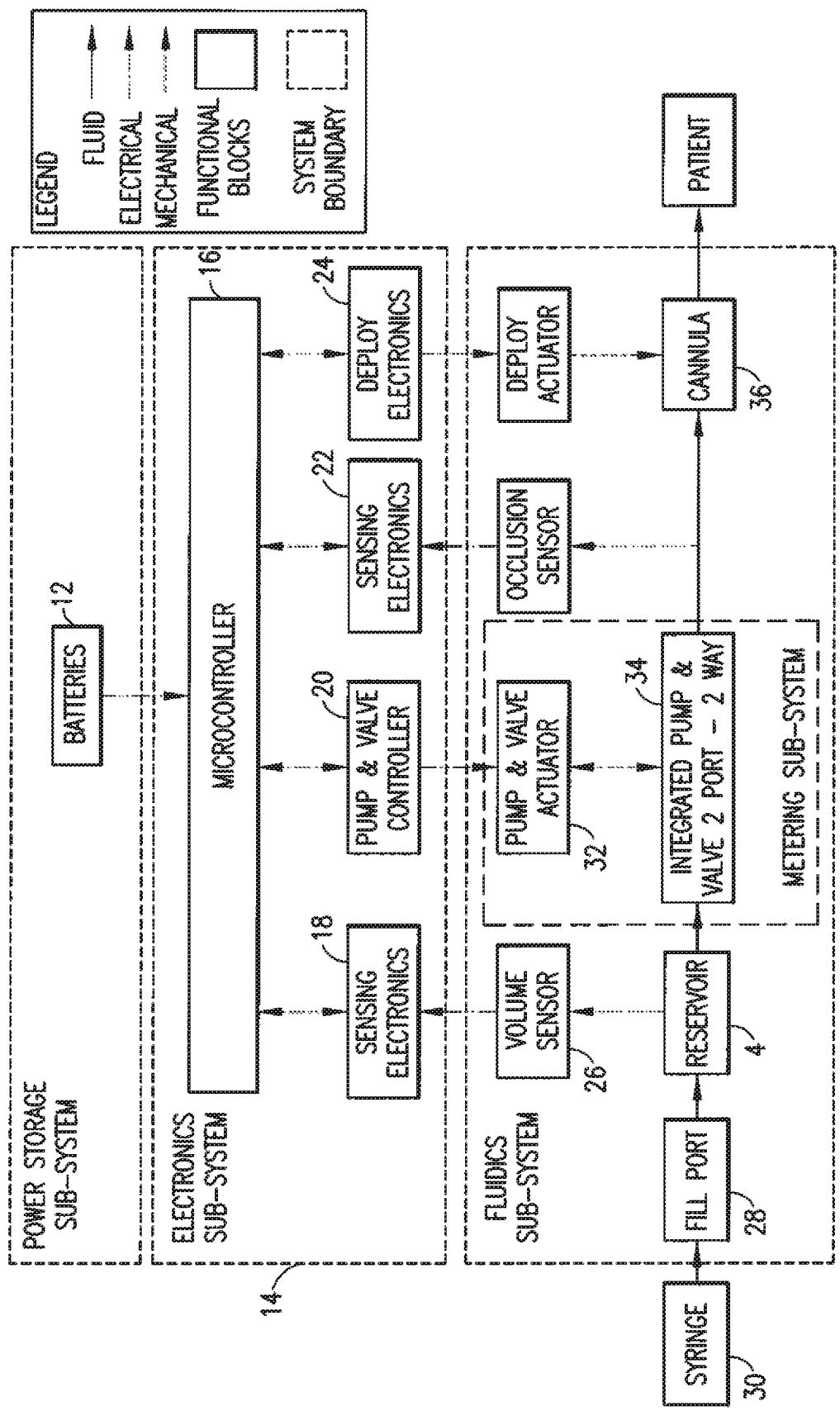
FIG. 3 is a schematic view of a fluidic architecture and metering sub-system diagram of the delivery device of FIG. 1.

FIG. 3 is a patch-pump fluidic architecture and metering sub-system diagram of a patch pump. The power storage sub-system for the patch pump includes batteries 12. The control electronics 14 of the patch pump may include a microcontroller 16, sensing electronics 18, pump and valve controller 20, sensing electronics 22, and deployment electronics 24, which control the actuation of the patch pump. The patch pump includes a fluidics sub-system that may include the reservoir 4, volume sensor 26 for the reservoir 4, a reservoir fill port 28 for receiving a refill syringe 30 to refill the reservoir 4. The fluidics sub-system may include a metering system comprising a pump and valve actuator 32 and an integrated pump and valve mechanism 34. The fluidics sub-system may further include an occlusion sensor, a deployment actuator, as well as the cannula 36 for insertion into an infusion site on the user's skin. The architecture for the patch pumps is the same or similar to that which is illustrated in FIG. 1.

With reference to FIG. 1, the wearable medical delivery device (e.g., insulin delivery device (IDD) such as patch pump 1 is operable in conjunction with a remote controller that preferably communicates wirelessly with the pump 1 and is hereinafter referred to as the wireless controller (WC). The WC can comprise a graphical user interface (GUI) display for providing a user visual information about the operation of the patch pump 1 such as, for example, configuration settings, an indication when a wireless connection to the patch pump is successful, and a visual indication when a dose is being delivered, among other display operations. The GUI display can include a touchscreen display that is programmed to allow a user to provide touch inputs such as a swipe to unlock, swipe to confirm a request to deliver a bolus, and selection of confirmation or settings buttons, among other user interface operations.

The WC can communicate with the delivery device (e.g., patch pump 1) using any one or more of a number of communication interfaces. For example, a near field radiation interface is provided to synchronize the timing of the WC and patch pump 1 to facilitate pairing upon start up. Another interface can be provided for wireless communication between the WC and the patch pump 1 that employs a standard Bluetooth Low Energy (BLE) layer, as well as Transport and Application layers. Non-limiting examples of Application layer commands include priming, delivering basal dose, delivering bolus dose, cancelling insulin delivery, checking patch pump 1 status, deactivating the patch pump 1, and patch pump 1 status or information reply.

Figure 4:
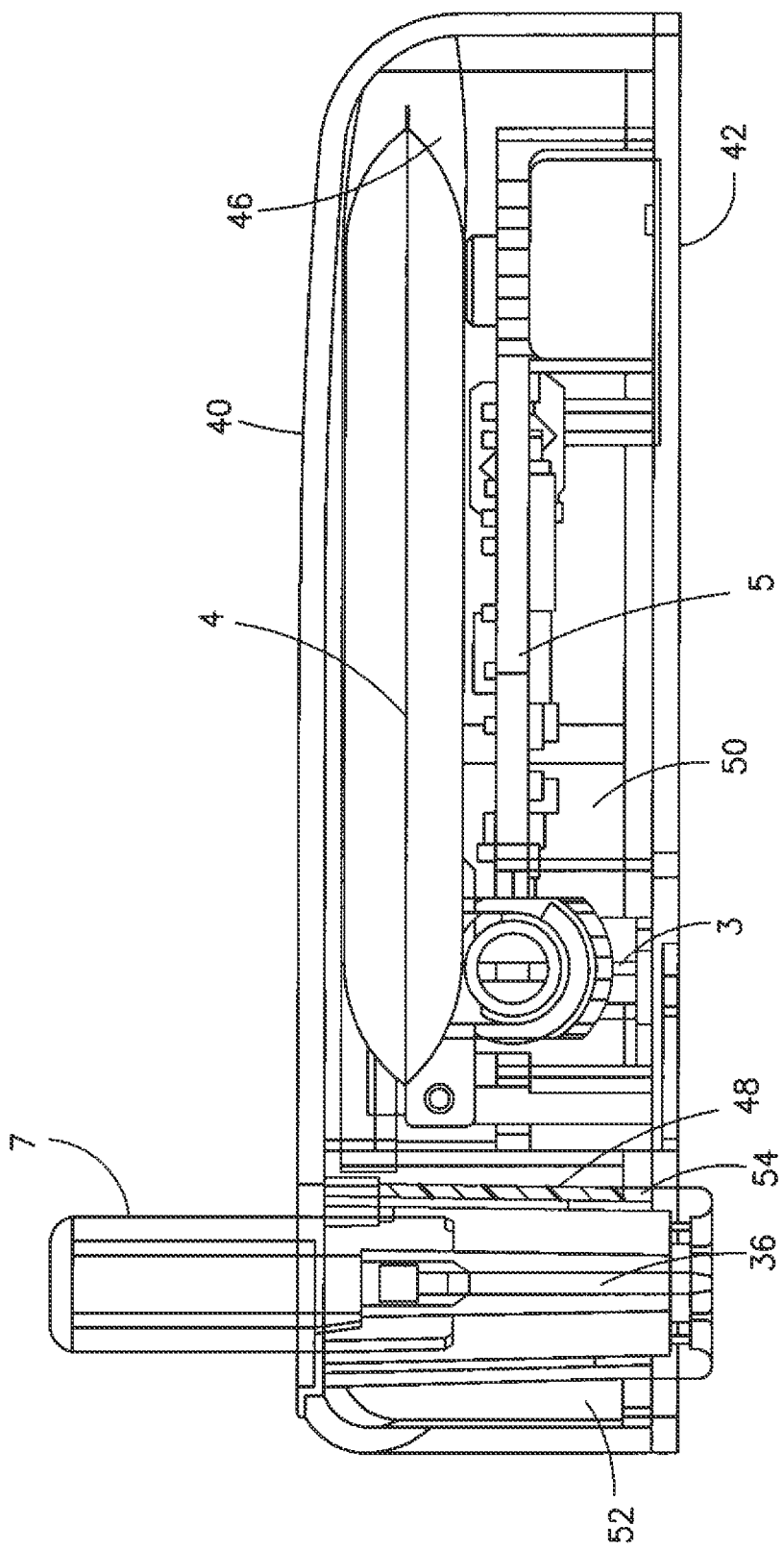
FIG. 4 is a cross-sectional view of the delivery device of FIG. 1.

FIG. 4 is a cross-sectional view of a patch pump 1 according to an exemplary embodiment. The patch pump 1 has a housing 40, which forms a main cover that can be liquid sealed or, preferably, hermetically sealed to a base 42. The base 42 carries various components as described below in detail. The hermetic seal between the housing 40 and the base 42 prevents fluid ingress and prevents other particles from passing the seal. Embodiments of the patch pump 1 also include a vent 44 shown in FIGS. 6 and 7 or a vent membrane to provide pressure equalization between the interior of the housing 40 and the exterior atmosphere.

Embodiments of the seal between the housing 40 and the base 42 include, for example, a liquid-tight seal, an O-ring seal or another mechanical seal, a gasket, an elastomer, a heat seal, an ultra-sonically welded seal, a laser weld, chemical joining, an adhesive, a solvent weld, or an adhesive weld. Laser welding is the preferred sealing method because, when laser welding is properly performed, a seamless fully hermetic seal is formed. The vent 44 or the vent membrane continues to have the functional purpose of equalizing internal pressure and providing a sterile environment. One skilled in the art will appreciate that other seals can be used without departing from the scope of the present disclosure.

Referring to FIG. 4, the housing 40 and the base 42 define an interior 46 divided by a wall forming a barrier 48 into a first internal region 50 and a second internal region 52. According to one embodiment, the barrier 48 is a part of the housing 40 and is integrally formed as a unitary structure with the housing. The barrier 48 is preferably sealed to a protruding rib 54 on the base 42 such that the interface between the barrier 48 and the rib 54 is hermetically joined using an appropriate sealing method. The barrier 48 separates the first internal region 50 from the second internal region 52 and protects the first internal region 50 from fluid ingress from the second internal region. According to one embodiment, the second internal region 52 is not sealed from fluid ingress.

The first internal region 50 includes components such as the pump 3, the force sensing resistor 32, and the electronics 18. Examples of the electronics include semiconductor chips, controllers, diodes, antennas, coils, batteries, discrete components (resistors and capacitors, for example) and circuit boards used to operate and control the patch pump 1 and operate the pump 3. As readily understood by the skilled artisan, it is desirable to have a dry environment for proper operation of these components, particularly the electronics 18. The second internal region 52 includes the insertion mechanism 7 and the cannula 36. According to one embodiment, because the insertion mechanism 7 interfaces with the skin of a patient, the second internal region 52 can be neither a hermetically sealed environment, nor a liquid-tight environment.

According to one embodiment, the components of the first internal region 50 are different from the components of the second internal region 52. Alternatively, the first internal region 50 and the second internal region 52 share some of the same components. For example, in some embodiments, portions of the reservoir 4 are disposed in both the first and second internal regions. When the reservoir and the insertion mechanism 7 are separated by the barrier 48, the two internal regions fluidly communicate for effective operation of the patch pump 1 and transfer of fluid from the reservoir and the pump mechanism.

Figure 5:
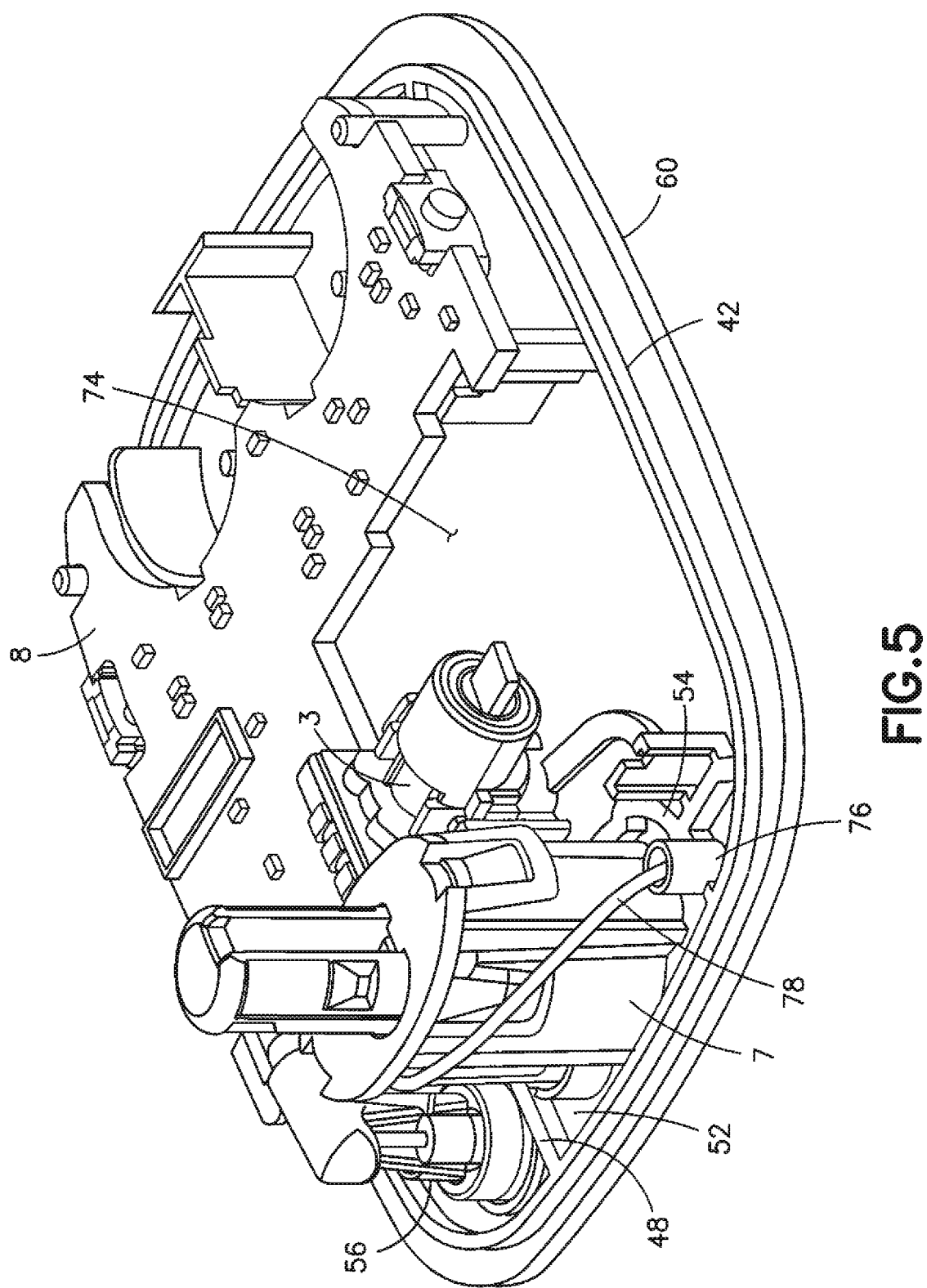
FIG. 5 is a perspective view of the delivery device of FIG. 4, omitting a cover and a reservoir for clarity.

FIG. 5 illustrates some of the main components of the patch pump 1 in a perspective view with the main cover and the reservoir 4 removed for clarity. According to one embodiment, a fill port 56 is connected to a conduit for supplying the medicament to the reservoir 4. The fill port 56 can be disposed in the first internal region 50 or the second internal region 52, but is typically located in the first internal region 50. In some embodiments, the fill port 56 includes a portion that serves as part of the flow path for medicament exiting the reservoir 4.

Figure 6:
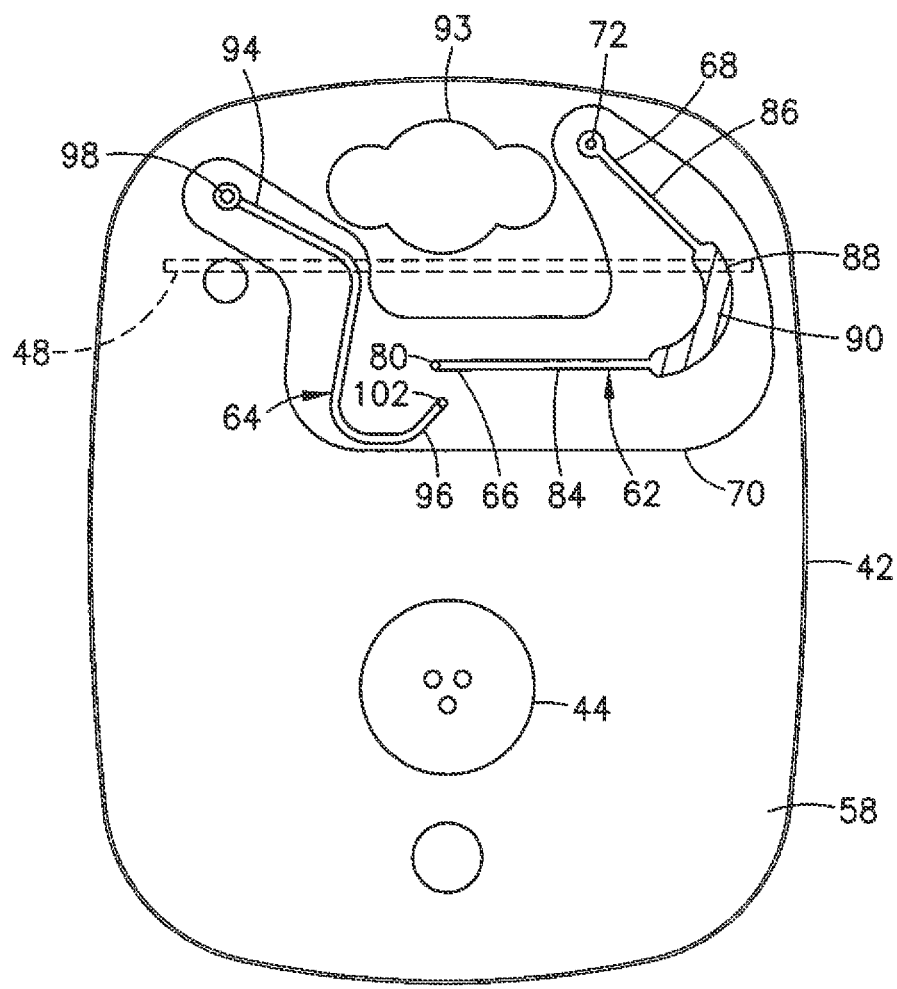
FIG. 6 is a bottom view of the base of the delivery device of FIG. 1 with the components removed.

FIG. 6 illustrates a bottom surface 58 of the base 42 of the patch pump 1. During use, the bottom surface 58 is oriented toward the skin of the patient. In some embodiments, the bottom surface 58 includes an adhesive that removably attaches the base to the skin of the patient. Alternatively, an adhesive pad 60, as illustrated in FIG. 1, adheres to both the bottom surface 58 and the skin of the patient. Typically, 3M™ medical tape (e.g. product no. 1776) is the adhesive used, although various types of known industry adhesives can be used. The adhesive is selected to ensure compatibility with human skin to prevent undesired reactions. Also, compatibility of the adhesive and the insulin is considered in case that the adhesive and the insulin accidentally mix.

Figure 7:
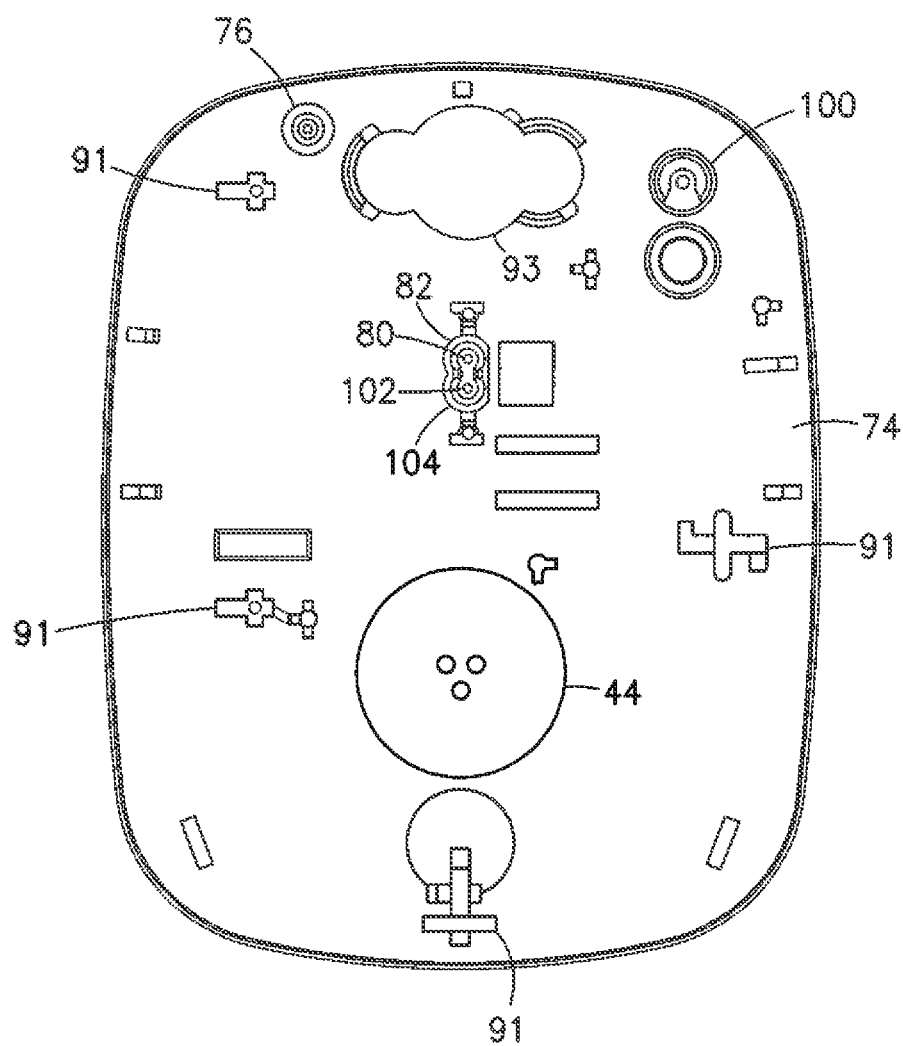
FIG. 7 is a top view of the base of the delivery device of FIG. 1 with the components removed.

As shown in FIG. 6, the bottom surface 58 of the base 42 includes at least one recess for forming a fluid channel through the base 48 from a first location to a second location. The recess forming the fluid channel can have a substantially U-shape or groove shape with a longitudinal dimension and an open side facing outward from the bottom surface 58. In the embodiment shown, a first fluid channel 62 and second fluid channel 64 are provided. The fluid channels extend in a longitudinal direction parallel to the plane of the base 42 and are configured and located to direct a fluid from one location in the device to a second location in the device. In the embodiment shown, the first fluid channel 62 is formed by a recess having an inlet end 66 and an outlet end 68. The first fluid channel 62 is typically molded in the bottom surface 58 and covered by a cover member 70 to enclose the channel and form a fluid tight path for the fluid passing through the channel. The cover 70 can be a thin flexible membrane, sheet, or film bonded to the bottom surface 58 to overly and cover the channel as shown in FIG. 6 to form a fluid tight path for the medicament. As shown in FIG. 7, the outlet end 68 of the channel 62 includes an opening 72 passing through the base 42 between the bottom surface 58 and a top surface 74. A coupling 76 is formed on the top surface 74 where the opening passes through the coupling. The coupling 76 has an open end portion for receiving a flexible conduit 78 as shown in FIG. 5. In the embodiment shown, the conduit 78 extends between the outlet end 68 of the channel 62 to the cannula 36 of the insertion mechanism for supplying the cannula with the medicament and delivering to the patient. As used herein the cannula refers to the delivery device having a lumen for introducing the medicament into the patient. The cannula can be hollow steel cannula or a flexible catheter as known in the art.

The inlet end 66 of the channel 62 also include an opening 80 extending between the bottom surface 58 and the top surface 74 forming fluid path between the top surface and the bottom surface. A coupling 82 is on the top surface 74 communicating with the opening 80 and the channel 62. In the embodiment shown, the coupling 82 receives a conduit that extends between the pump 32 and the channel 62 for supplying the medicament through the channel. In the embodiment shown, the channel 62 extends parallel to a plane of the base 42 with fluid openings in the top face 74 of the base 42 for directing the fluid between two spaced-apart locations on the top face of the base. The channel 62 is located and has a length to provide fluid communication between the operating components of the delivery device located in the cavity of the housing 40. In one embodiment, the channel 62 is oriented or positioned so that the inlet end 66 and the outlet end 68 are on opposite side of the barrier 48 to provide fluid communication between the first internal region 50 and the second internal region 52.

Referring to FIG. 6, the channel 62 has a first section 84 and a second section 86 and an enlarged recessed area 88 between the first section 84 and the second section 86, The first and second sections have a first internal diameter sufficient to carry the medicament, such as insulin, to the cannula 36 at a rate effective for introducing the medicament to the patient. The recessed area 88 in the embodiment shown has a larger cross section and diameter than the first and second sections. A filter media 90 is included in the recessed area and fills the recessed area with a sufficient amount to filter and/or treat the fluid passing through the channel 62.

The filter media 90 can include or contains an adsorbent material that is able to adsorb and remove at least a portion of one or more components from the fluid passing through the channel 62. Examples of a suitable adsorbent material include carbon materials, charcoal, activated charcoal, activated carbon and mixtures of these. The activated carbon can be obtained by pyrolysis in an inert atmosphere or by chemical activation. The filter media 90 can be an adsorbent in the form of beads, powder, pellets or extruded shapes. The filter media 90 can be made of the adsorbent material or can be a support structure including or containing an adsorbent material. The adsorbent is able to remove a sufficient amount of stabilizers in a medication to inhibit irritation and/or inflammation at the delivery site in the patient without impeding or restricting the flow of the medication through the channel under normal operating conditions of the pump.

The delivery device is particularly suitable for delivering insulin to the patient over an extended period of time. The delivery device is actuated to insert the cannula 36 into the patient. The pump is actuated to carry the insulin from the reservoir 4 to the cannula 36 where the insulin is introduced into the patient. Insulin solutions typically include stabilizing and preservative agents and compounds to extend the useful life of the insulin prior to introducing to the patient. Commonly used preservative and stabilizing agents include phenol and m-cresol that are effective in extending the shelf life of insulin. Phenol, m-cresol and other stabilizing agents while effective in stabilizing the insulin often cause irritation and inflammation at the infusion site after a period of time and prolonged use. Infusion devices, such as patch pumps, that provide a sustained delivery of insulin for several days are particularly prone to irritation and inflammation at the infusion site that can be caused by the stabilizing compounds in the insulin solution. The irritation and inflammation are the infusion site can result in loss of absorption in the insulin and reduced effectiveness for maintaining the desired insulin and glucose levels in the patient. The adsorbent is selected to remove at least a portion of the stabilizing agent without interference with the effectiveness of the insulin.

In embodiments of the device, the adsorbent is provide or positioned in the fluid path of the insulin to remove the stabilizing agents prior to introducing the insulin to the patient within a time where the absence of the stabilizing agent in the insulin does not cause degradation of the insulin before introducing to the patient. In the embodiment shown, the adsorbent is located between the pump and the cannula to contact the insulin and remove at least a portion of the stabilizing agents prior to supplying the insulin to the cannula and prior to introducing to the patient. Alternatively, the adsorbent can be positioned before or upstream of the pump mechanism. By reducing the amount of the stabilizing agent, such as phenol and/or m-cresol from the insulin immediately or just prior to introducing to the patient, the occurrence of irritation and inflammation caused by the stabilizing agent at the delivery or infusion site can be reduced and/or inhibited. Preferably, the adsorbent reduces the concentration of the stabilizing agent present in the insulin to reduce or eliminate the irritation at the infusion site caused by the stabilizing agent. The adsorbent is located near the cannula or catheter so that insulin is delivered to the patient within a time where decomposition of the insulin is minimized. In one embodiment, the adsorbent can remove all or a substantial portion of the stabilizing agent from the insulin. The amount of the stabilizing removed from the insulin can be controlled by the specific adsorbent, the volume or amount of the adsorbent relative to the volume of the insulin passing through the channel, the contact time of the insulin with the adsorbent and the rate of flow of the insulin through the adsorbent. Typically, the adsorbent is able to remove an amount of the phenol or m-cresol or other stabilizing agent to inhibit irritation and/or inflammation caused by phenol or m-cresol at the delivery site in the patient.

The recessed area 88 preferably contains a sufficient amount of the adsorbent in the flow path of the channel 62 so that the medicament, such as the insulin, passes through the adsorbent before passing to the cannula. The channel is shown as having the enlarged recessed area between the first and second sections. In other embodiments, the recessed area and the adsorbent can be located at the outlet end or at the inlet end of the channel 62. In further embodiments, the entire channel can be filled with the adsorbent and the channel can have a uniform width or diameter extending between the inlet end and the outlet end. The cover member 70 is attached to the bottom face of the base 42 to retain the adsorbent in the recessed area and define the flow path for the fluid through the channel 62. The filter media and/or adsorbent typically has a porosity to remove an amount of the stabilizing agent effective to inhibit inflammation at the insulin delivery site.

As shown in FIG. 7, the top face 74 of the base 42 is formed with various posts and mounting structures 91 for supporting the various operating components of the delivery device, such as the pump, printed circuit board, reservoir and the like as shown in FIGS. 4 and 5. An opening 93 is shown at one end for receiving the cannula insertion mechanism 7. The components of FIG. 4 and FIG. 5 are not shown for clarity.

Figure 8:
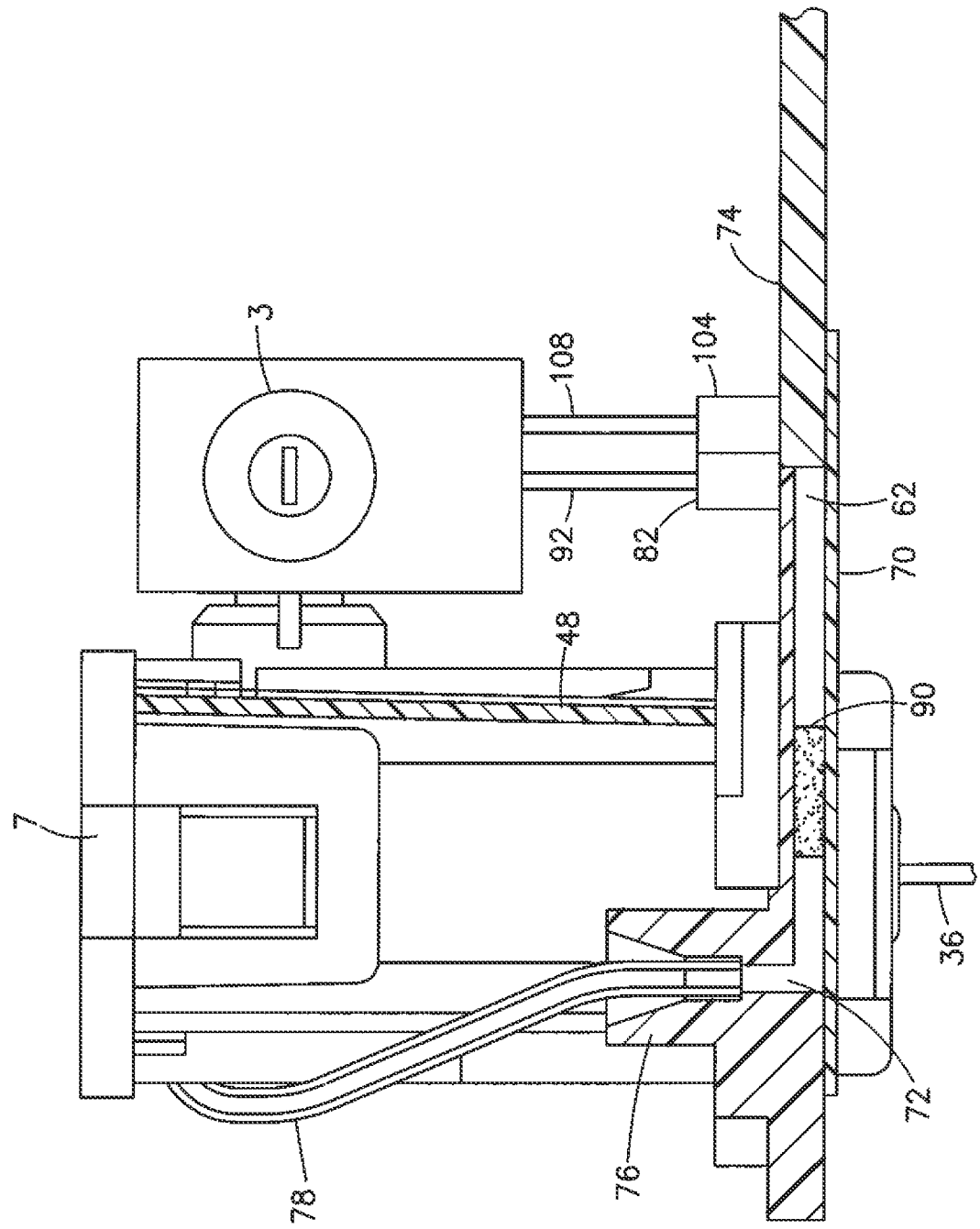
FIG. 8 is a partial cross-sectional view the delivery device showing the fluid channel.

FIG. 8 is a side view in partial cross-section of the delivery device showing the channel 62 enclosed by the cover member 70 and the filter media 90 including the adsorbent contained in the fluid path of the channel 62. The coupling 76 is shown connected to the flexible conduit 78 leading to the insertion mechanism and the cannula. In FIG. 8, the insertion mechanism is shown in the actuated position and the cannula 36 inserted into the skin of the patient. The coupling 82 at the inlet end of the channel 62 is shown connected to a conduit 92 extending to the pump 32. The filter media and the adsorbent 90 in this embodiment is positioned between the pump 32 and the cannula 36 so that the medicament, such as the insulin, passes through the adsorbent before reaching the cannula to remove at least a portion of the stabilizing agent before introducing the insulin to the patient. As shown in FIG. 8, the fluid channel extends below the barrier wall 48 between the first interior region 50 and the second interior region 52. In this manner, the fluid channel is able to carry the fluid or medication between the regions 50 and 52 without passing directly through the barrier 48.

Figure 9:
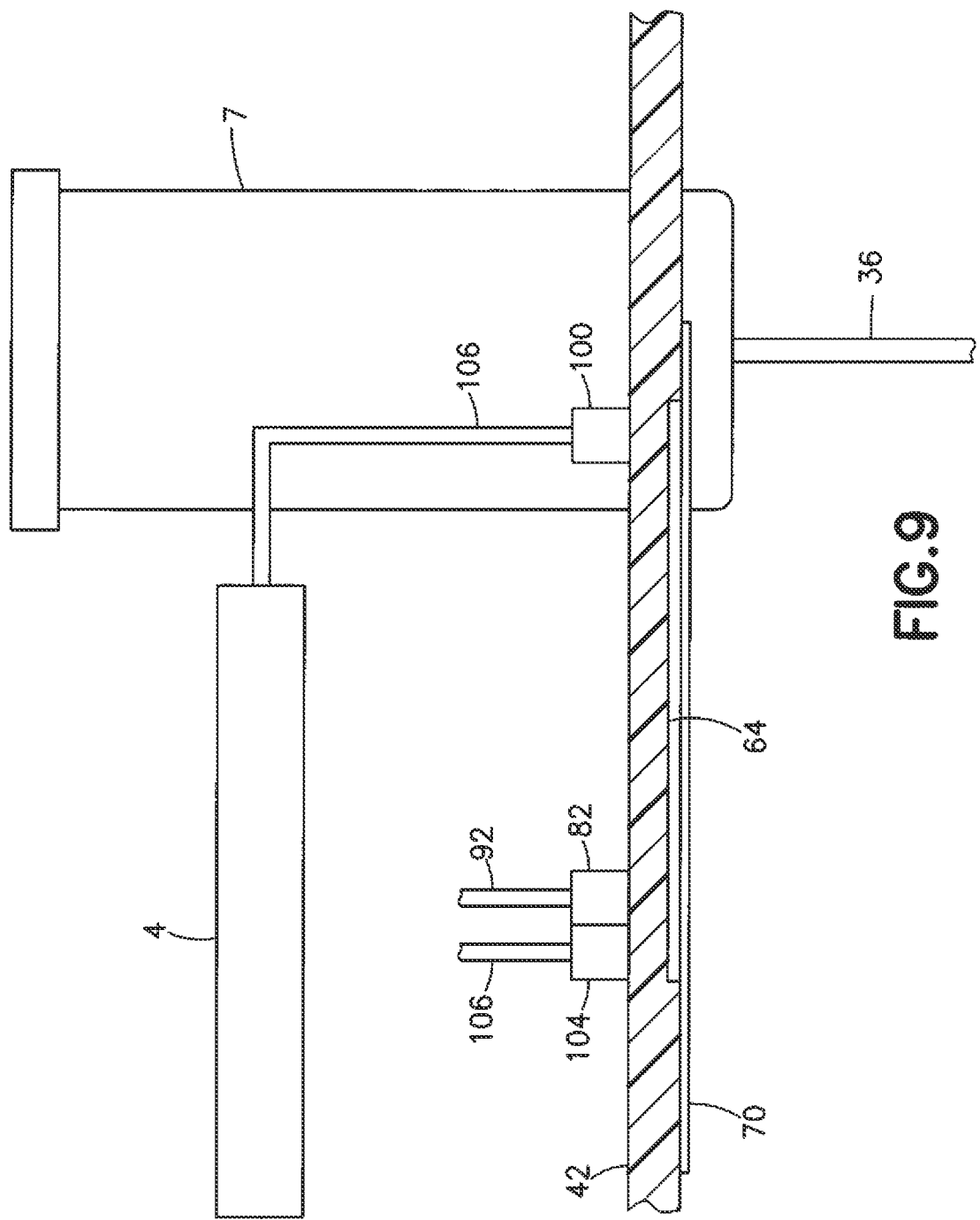
FIG. 9 is a partial cross-sectional view of the delivery device showing the fluid channel connected to the reservoir.

The second channel 64 shown in FIG. 6 is also formed in the bottom surface 58 of the base 42 and is formed with an inlet end 94 and an outlet end 96. The second channel 64 is molded into the bottom face to have a dimension sufficient to carry the medicament, such as the insulin, from one location to another location within the device and from one operating component to another component. The channel 64 has an opening 98 at the inlet end 94 extends through the base 42 to the top surface to a coupling 100. The outlet end includes an opening 102 extending through the base 42 to a coupling 104. As shown in FIG. 9, the cover member 70 overlies the channel 64 to enclose the channel. The cover 70 is shown as a single film covering the channels 62 and 64. Alternatively, each channel 62 and 64 can be enclosed by a separate cover member. A conduit 106 extends between the coupling 100 and the reservoir 4 to carrier the medicament from the reservoir to the channel 64. The conduit 108 is connected to the coupling 104 at the outlet end of the channel 64, which is connected to the pump. In use, the pump is operated to pump the medicament from the reservoir 4 though the conduit 106 through the channel 64 and through the conduit 108 to the pump. The pump then directs the medicament through the conduit 92 to the first channel 62 and through the adsorbent of the filter media 90 where the treated medicament is directed through the conduit 78 connected to the cannula. The treated medicament is then directed to the cannula for delivering to the patient.

Figure 10:
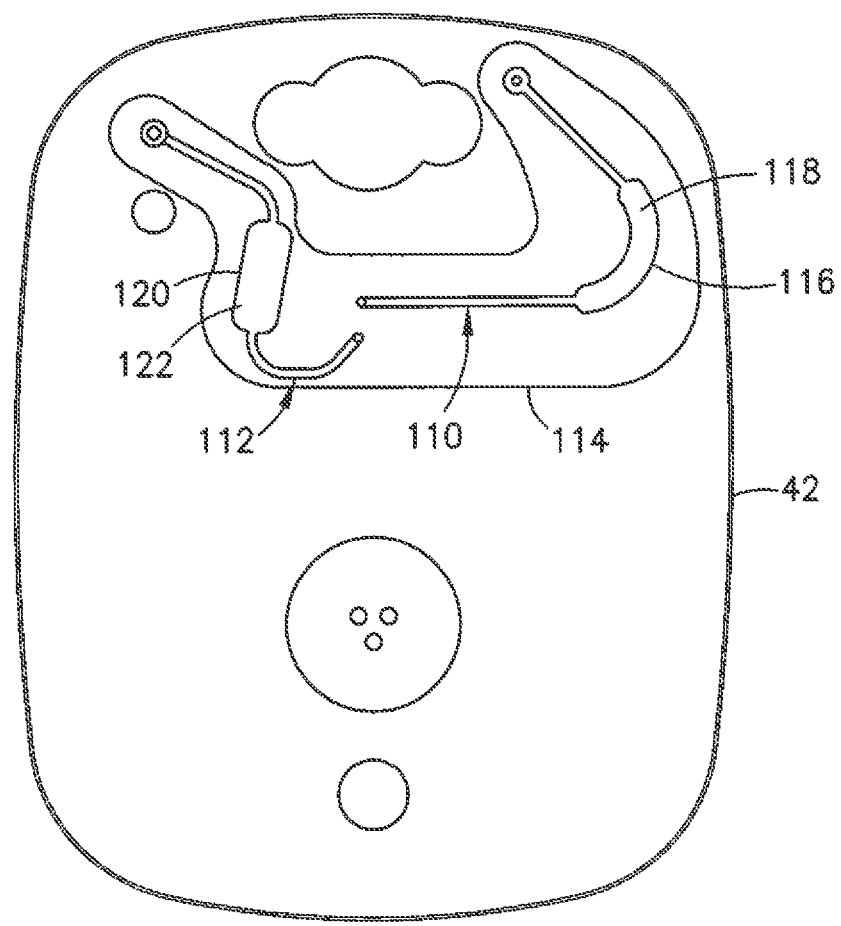
FIG. 10 is a top view of the base of the delivery device in another embodiment.

In another embodiment shown in FIG. 10, the bottom face of the base 42 includes fluid channels 110 and 112 formed in the bottom face of the base 42 in a manner similar to the embodiment of FIG. 6. The fluid channels 110 and 112 are in fluid communication with the reservoir, pump and cannula as in the previous embodiment to carry the medicament from the reservoir to the cannula. A cover member 114 is applied over the channels to enclose the fluid channel for directing the fluid through the channels. In the embodiment shown, the channel 110 includes a recessed area 116 including a filter media containing an adsorbent 118 so that the fluid medicament passing through the channel 110 contacts the adsorbent to remove a portion of the stabilizer compounds in the medicament. As in the previous embodiment, the channel 110 is in fluid communication with the pump and the cannula for directing the treated fluid to the cannula. The second channel 112 is formed in a similar manner and includes an enlarged recessed area 120 for the filter media 122 containing the adsorbent. The second channel 112 is in fluid communication with the pump and reservoir as in the previous embodiment to treat the fluid medicament after removing from the reservoir and before conveying to the cannula for delivery to the patient.

The fluid channels are recessed from (or inscribed into) the bottom surface of the base by a molding process, such as injection molding, or by a cutting process, such as milling. In other embodiments, the fluid channels are disposed on the main cover of the housing, or on the base 42 within the inner cavity of the housing 40. Similar fluid channels can be positioned in a plurality of locations in the device.

The cross-sectional shape and dimension of the fluid channels is defined by the desired flow characteristics. The geometry of the flow channels is selected based on factors such as cost, manufacturing capability, and desired use. Exemplary cross-sectional profiles of the fluid channels include square, rectangular, and semi-circular. One skilled in the art will appreciate that other cross-sectional profiles can be used without departing from the scope of the present invention.

Preferably, the fluid channels are sized to allow unrestricted medicament fluid flow. The pump connected to the fluid channels controls and determines the medicament fluid flow rate, instead of the size of the fluid channels. When the fluid channels are too small, capillary action can occur, potentially resulting in the obstruction of medicament fluid flow. Preferably, the cross-sectional area of the fluid channels is greater than the gage of the cannula 36.

In one embodiment, the film channel cover 70 is made of foil available from Oliver-bolas Healthcare Packaging (e.g., TPC-0777A foil). Preferably, the film channel cover 70 is made of Oliver-Tolas Healthcare Packaging IDT-6187 clear film and is heat sealed or heat staked to the bottom surface of the base 42 to enclose the fluid channels. Laser welding, for example, applies laser light through the clear film to fix the film channel cover 70 to the bottom surface of the base 42. Laser welding is advantageous because a laser can straddle the channel edge of the fluid channels during the welding process and adhere the film to the base 42 in areas that are closer to the channel edges than other methods.

The sealed fluid channel cover 70 encloses and protects the medicament from contamination while travelling through the fluid channels. When the fluid channels are disposed in the inner cavity of the housing 42 as described above, one or more fluid channel covers 70 can be appropriately disposed in the top face of the base 42.

According to one embodiment, the medicament exits the first internal region 50 of the housing 40 via the opening in the base 42, entering the first fluid channel 62 in the bottom surface 58 of the base 42. Subsequently, via the fluid channel passageway disposed at the first end of the first fluid channel 62, the medicament passes to the interior of the housing 40 into the second internal region 52. By routing the medicament through the first fluid channel 62 outside the interior of the housing, the first fluid channel 62 advantageously and effectively bypasses the barrier 48. The first fluid channel establishes fluid communication between the pump 3 and the cannula 47 while bypassing the barrier 49, thereby maintaining the integrity of the barrier 48. The first fluid channel 62 provides fluid communication between the first internal region 50, which is sealed from fluid ingress, and the second internal region 52, which is not sealed from fluid ingress without compromising the integrity of the barrier 48.

Although only a few embodiments of the present device are shown and described, the present device is not limited to the described embodiments. Instead, it will be appreciated by those skilled in the art that changes may be made to these embodiments without departing from the principles and spirit of the device. Different embodiments can be combined with other embodiments as long as they are not inconsistent with each other. It is particularly noted that those skilled in the art can readily combine the various technical aspects of the various elements of the various exemplary embodiments that have been described above in numerous other ways, all of which are considered to be within the scope of the disclosure and equivalents thereof.

The invention claimed is:

1. A delivery device for a medicament comprising:
a housing having an open end and an interior cavity;
a base coupled to said open end of said housing;
a reservoir within said cavity for containing the medicament;
a delivery mechanism for delivering the medicament to a patient;
a pump mechanism for delivering the medicament from the reservoir to the delivery mechanism;
said base having an integrally formed fluid channel in a bottom surface of said base opposite said interior cavity, said fluid channel having a flow path in fluid communication with said reservoir and said delivery mechanism, said fluid channel having a first inner dimension and having a recess having a second inner dimension, said second inner dimension being greater than said first inner dimension; and
a filter media comprising an adsorbent positioned in said recess of said fluid channel between said reservoir and said delivery mechanism for contacting the medicament and removing at least a portion of a compound from the medicament before delivering said medicament to said delivery mechanism, wherein said adsorbent is selected from the group consisting of carbon, charcoal, activated charcoal, activated carbon, and mixtures thereof.

2. The delivery device according to claim 1, wherein said compound of the medicament is a stabilizing agent, and where said filter media removes at least a portion of said stabilizing agent from said medicament before delivering said medicament to said patient.

3. The delivery device according to claim 2, wherein said medicament is an insulin solution and where said stabilizing agent is selected from the group consisting of m-cresol, phenol, and mixtures thereof, and where said filter media is included in an amount effective to remove at least a portion of the stabilizing agent to inhibit irritation at a delivery side of the delivery mechanism.

4. The delivery device according to claim 1, wherein said base has a bottom face with an open channel, and a cover overlying and enclosing said open channel defining said fluid channel.

5. The delivery device according to claim 4, wherein said cover is a foil bonded to said bottom face of said base.

6. The delivery device according to claim 4, wherein said fluid channel has an inlet end in fluid communication with said pump mechanism, and an outlet end in fluid communication with said delivery mechanism, and where said filter media is positioned between said pump mechanism and said delivery mechanism.

7. The delivery device according to claim 6, wherein said delivery mechanism includes a cannula having a distal end for penetrating the skin of the patient, and a proximal end, and a conduit extending between said proximal end of said cannula and said outlet end of said fluid channel.

8. The delivery device according to claim 7, wherein said filter media is positioned in said fluid channel between said cannula and said pump mechanism.

9. The delivery device of claim 4, wherein said fluid channel has a first section with a first inner diameter and said recess has a second inner diameter greater than said first inner diameter, and where said filter media is positioned in said recess.

10. The delivery device of claim 1, wherein said fluid channel has a first section with a first inner diameter and a said recess has a second inner diameter greater than said first inner diameter, and where said filter media is positioned in said recess, and said channel extends between said pump mechanism and said delivery mechanism.

11. The delivery device of claim 1, wherein said fluid channel comprises a first channel formed in said bottom surface of said base and extending between said reservoir and said pump mechanism, said first channel having said recess containing said adsorbent for removing a preservative from said medicament before supplying said medicament to said delivery mechanism, and a second channel formed in said bottom surface and extending between said pump mechanism and said delivery mechanism, said second channel having a recess containing said adsorbent for removing said preservative from said medicament before supplying said medicament to said delivery mechanism.

12. A delivery device for a medicament comprising:
a housing having an open end and an interior cavity;
a base coupled to said open end of said housing;
a reservoir within said cavity for containing the medicament;
a delivery mechanism for delivering the medicament to a patient;
a pump mechanism for delivering the medicament from the reservoir to the delivery mechanism;
said base having an integrally formed open fluid channel in a bottom surface of said base opposite said interior cavity, a cover overlying and enclosing said open fluid channel, said fluid channel having a flow path in fluid communication with said reservoir and said delivery mechanism, wherein said housing further comprises a barrier wall defining a first interior region and a second interior region, and where said fluid channel extends between said first interior region and said second interior region; and
an adsorbent positioned in said fluid channel between said reservoir and said delivery mechanism for contacting the medicament and removing at least a portion of a compound from the medicament before delivering said medicament to said delivery mechanism, wherein said adsorbent is selected from the group consisting of carbon, charcoal, activated charcoal, activated carbon, and mixtures thereof.

13. A delivery device for delivering a medicament to a patient, said delivery device comprising:
a housing having an interior cavity and a base enclosing said cavity; said base having an integrally formed fluid channel in a bottom surface of said base opposite said cavity and having an inlet and an outlet, said fluid channel having a first inner dimension and having a recess having a second inner dimension, said second inner dimension being greater than said first inner dimension, and said recess being between said inlet and said outlet;
a reservoir within said cavity for containing the medicament, where said medicament contains a stabilizing agent, and where said reservoir is in fluid communication with said inlet of said fluid channel;

a delivery mechanism having a cannula for delivering the medicament to the patient, wherein said cannula is in fluid communication with said outlet of said fluid channel;

a pump in fluid communication with said cannula for directing the medicament from said reservoir to said cannula; and an adsorbent in said recess of said fluid channel in the bottom surface of said base between said reservoir and said delivery mechanism, wherein said medicament passing through said fluid channel contacts said adsorbent to remove at least a portion of said stabilizer compound from said medicament.

14. The delivery device according to claim 13, wherein said medicament is an insulin solution and said stabilizing agent is selected from the group consisting of m-cresol, phenol, and mixtures thereof, and where said adsorbent is included in an amount effective to remove at least a portion of the stabilizing agent to inhibit irritation at a delivery side of the delivery mechanism.

15. The delivery device according to claim 13, wherein said adsorbent is selected from the group consisting of carbon, charcoal, activated charcoal, activated carbon, and mixtures thereof, and where said adsorbent is included in an amount to remove at least a portion of said stabilizing agent passing through said fluid channel.

16. The delivery device of claim 13, wherein said base has an inner surface facing said cavity and said bottom surface having an open channel defining said fluid channel, and a cover overlying and enclosing said open channel to form said fluid channel.

17. The delivery device according to claim 16, wherein the cover comprises a foil attached to the base.

18. The delivery device according to claim 16, wherein said base has a first coupling with a fluid passage in communication with said inlet of said fluid channel and a conduit coupled to said first coupling, and a second coupling with a fluid passage in communication with said outlet of said fluid channel and a conduit coupled to said second coupling and connected to said cannula, and where said adsorbent is positioned in the fluid channel between said pump and said cannula for removing at least a portion of the stabilizer compound from said medicament.

19. The delivery device according to claim 13, wherein said inlet of said fluid channel is in fluid communication with said pump, and said outlet is in fluid communication with said cannula.

20. The delivery device according to claim 13, wherein said fluid channel has a first section with a first inner diameter and—a said recess with a second inner diameter greater than said first diameter, and where said adsorbent is disposed in said recess.

21. The delivery device of claim 13, wherein said fluid channel comprises a first channel formed in said bottom surface of said base and extending between said reservoir and said pump, said first channel having said recess containing said adsorbent for removing a preservative from said medicament before supplying said medicament to said delivery mechanism, and a second channel formed in said bottom surface and extending between said pump mechanism and said delivery mechanism, said second channel having a recess containing a second adsorbent for removing said preservative from said medicament before supplying said medicament to said delivery mechanism.

22. An insulin delivery device for delivering insulin to a patient where said insulin includes a phenolic preservative, said delivery device comprising:

a housing having an interior cavity, the housing having a base with an integral fluid channel formed in a bottom surface of said base opposite said cavity, said fluid channel having a first inner cross sectional dimension and having a recess having a second inner cross sectional dimension, said second inner cross sectional dimension being greater than said first inner cross sectional dimension, and an adsorbent in said recess of said fluid channel to contact the insulin; and a delivery mechanism for delivering the insulin to a patient, wherein said fluid channel is in fluid communication with said delivery mechanism for delivering the insulin to the delivery mechanism, and where the insulin passes through said adsorbent to remove at least a portion of stabilizer compounds in the insulin before delivering the insulin to the delivery mechanism.

23. The insulin delivery device according to claim 22, wherein said base has an outer surface with an open channel and a cover overlying and enclosing said open channel to define said fluid channel, and wherein said housing further comprises a barrier wall defining a first interior region and a second interior region, and where said fluid channel extends between said first interior region and said second interior region.

24. The insulin delivery device according to claim 22, wherein said fluid channel extends between a pump mechanism and the delivery mechanism to remove the preservative from the insulin before reaching said delivery mechanism, and where said recess of said fluid channel a diameter greater than a diameter of said fluid channel.

25. The insulin delivery device of claim 22, wherein said fluid channel comprises a first channel formed in said bottom surface of said base and extending between a reservoir and a pump mechanism, said first channel having said recess containing said adsorbent for removing-a said preservative from said insulin before supplying said insulin to said delivery mechanism, and a second channel formed in said bottom surface and extending between said pump mechanism and said delivery mechanism, said second channel having a recess containing said adsorbent for removing said preservative from said insulin before supplying said insulin to said delivery mechanism.

* * * * *